United States Patent
Anderson (10) Patent No.: US 8,391,952 B2
(45) Date of Patent: Mar. 5, 2013

(54) COIL ARRANGEMENT FOR AN ELECTROMAGNETIC TRACKING SYSTEM

(75) Inventor: Peter Traneus Anderson, Andover, MA (US)

(73) Assignee: General Electric Company, Schenectady, NY (US)

( * ) Notice: Subject to any disclaimer, the term of this patent is extended or adjusted under 35 U.S.C. 154(b) by 1312 days.

(21) Appl. No.: 11/870,854

(22) Filed: Oct. 11, 2007

(65) Prior Publication Data
US 2009/0096443 A1    Apr. 16, 2009

(51) Int. Cl.
*A61B 5/05*    (2006.01)

(52) U.S. Cl. ........ 600/424; 600/407; 600/410; 600/130; 324/245; 324/247; 702/150

(58) Field of Classification Search .................. 600/407, 600/410, 424, 130; 324/207, 247; 702/150
See application file for complete search history.

(56) References Cited

U.S. PATENT DOCUMENTS

| | | |
|---|---|---|
| 3,121,228 A | 2/1964 | Kalmus |
| 3,392,390 A | 7/1968 | Schelisch |
| 3,529,682 A | 9/1970 | Coyne et al. |
| 3,828,867 A | 8/1974 | Elwood |
| 3,868,565 A | 2/1975 | Kuipers |
| 3,983,474 A | 9/1976 | Kuipers |
| 4,054,881 A | 10/1977 | Raab |
| 4,314,251 A | 2/1982 | Raab |
| 4,613,866 A | 9/1986 | Blood |
| 4,618,822 A | 10/1986 | Hansen |
| 4,622,644 A | 11/1986 | Hansen |
| 4,642,786 A | 2/1987 | Hansen |
| 4,710,708 A | 12/1987 | Rorden et al. |
| 4,737,794 A | 4/1988 | Jones |
| 4,742,356 A | 5/1988 | Kuipers |
| 4,812,812 A | 3/1989 | Flowerdew et al. |
| 4,849,692 A | 7/1989 | Blood |
| 4,945,305 A | 7/1990 | Blood |
| 5,099,845 A | 3/1992 | Besz et al. |
| 5,172,056 A | 12/1992 | Voisin |

(Continued)

FOREIGN PATENT DOCUMENTS

| | | |
|---|---|---|
| WO | WO9736192 | 10/1997 |
| WO | WO9811504 | 3/1998 |

(Continued)

OTHER PUBLICATIONS

F. H. Raab, E. B. Blood, T. O. Steiner, and H. R. Jones, "Magnetic Position and Orientation Tracking System," IEEE Transactions on Aerospace and Electronic Systems, vol. AES-15, No. 5, pp. 709-718, Sep. 1979.

*Primary Examiner* — Brian Casler
*Assistant Examiner* — Joel Lamprecht
(74) *Attorney, Agent, or Firm* — Kenneth E. Horton; Kirton McConkie (57) ABSTRACT

An electromagnetic tracking system comprising at least one electromagnetic transmitter assembly or at least one electromagnetic receiver assembly with two coils attachable to a trackable object to be tracked. The two coils including a first large coil and a second small coil, with the second small coil positioned asymmetrically with respect to the first large coil. The electromagnetic tracking system enables a medical professional to continually track the position and orientation of the object during a medical procedure.

24 Claims, 4 Drawing Sheets

U.S. PATENT DOCUMENTS

| | | |
|---|---|---|
| 5,211,165 A | 5/1993 | Dumoulin et al. |
| 5,245,307 A | 9/1993 | Klaus et al. |
| 5,251,635 A | 10/1993 | Dumoulin et al. |
| 5,255,680 A | 10/1993 | Darrow et al. |
| 5,265,610 A | 11/1993 | Darrow et al. |
| 5,307,072 A | 4/1994 | Jones, Jr. |
| 5,307,808 A | 5/1994 | Dumoulin et al. |
| 5,377,678 A | 1/1995 | Dumoulin et al. |
| 5,437,277 A | 8/1995 | Dumoulin et al. |
| 5,443,066 A | 8/1995 | Dumoulin et al. |
| 5,445,150 A | 8/1995 | Dumoulin et al. |
| 5,453,686 A | 9/1995 | Anderson |
| 5,558,091 A | 9/1996 | Acker et al. |
| 5,592,939 A | 1/1997 | Martinelli |
| 5,600,330 A | 2/1997 | Blood |
| 5,640,170 A | 6/1997 | Anderson |
| 5,676,673 A | 10/1997 | Ferre et al. |
| 5,747,996 A | 5/1998 | Fuchs |
| 5,767,669 A | 6/1998 | Hansen et al. |
| 5,782,765 A | 7/1998 | Jonkman |
| 5,800,352 A | 9/1998 | Ferre et al. |
| 5,803,089 A | 9/1998 | Ferre et al. |
| 5,829,444 A | 11/1998 | Ferre et al. |
| 5,847,976 A | 12/1998 | Lescourret |
| 5,873,822 A | 2/1999 | Ferre et al. |
| 5,913,820 A | 6/1999 | Bladen et al. |
| 5,953,683 A | 9/1999 | Hansen et al. |
| 5,967,980 A | 10/1999 | Ferre et al. |
| 6,052,610 A | 4/2000 | Koch |
| 6,073,043 A | 6/2000 | Schneider |
| 6,129,667 A | 10/2000 | Dumoulin et al. |
| 6,129,668 A | 10/2000 | Haynor et al. |
| 6,161,032 A | 12/2000 | Acker |
| 6,172,499 B1 | 1/2001 | Ashe |
| 6,175,756 B1 | 1/2001 | Ferre et al. |
| 6,177,792 B1 | 1/2001 | Govari et al. |
| 6,188,355 B1 | 2/2001 | Gilboa |
| 6,201,387 B1 * | 3/2001 | Govari ..................... 324/207.17 |
| 6,201,987 B1 | 3/2001 | Dumoulin |
| 6,203,493 B1 | 3/2001 | Ben-Haim |
| 6,211,666 B1 | 4/2001 | Acker |
| 6,226,547 B1 | 5/2001 | Lockhart et al. |
| 6,230,038 B1 | 5/2001 | von Gutfeld et al. |
| 6,233,476 B1 | 5/2001 | Strommer et al. |
| 6,246,231 B1 | 6/2001 | Ashe |
| 6,266,552 B1 * | 7/2001 | Slettenmark .................. 600/424 |
| 6,285,902 B1 | 9/2001 | Kienzle, III et al. |
| 6,341,231 B1 | 1/2002 | Ferre et al. |
| 6,366,799 B1 | 4/2002 | Acker et al. |
| 6,369,564 B1 | 4/2002 | Khalfin et al. |
| 6,374,134 B1 * | 4/2002 | Bladen et al. ................. 600/424 |
| 6,377,041 B1 | 4/2002 | Jones, Jr. et al. |
| 6,400,139 B1 | 6/2002 | Khalfin et al. |
| 6,427,079 B1 | 7/2002 | Schneider et al. |
| 6,445,943 B1 | 9/2002 | Ferre et al. |
| 6,472,975 B1 | 10/2002 | Beigel et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,490,475 B1 | 12/2002 | Seeley et al. |
| 6,493,573 B1 | 12/2002 | Martinelli et al. |
| 6,516,213 B1 | 2/2003 | Nevo |
| 6,528,991 B2 | 3/2003 | Ashe |
| 6,534,982 B1 | 3/2003 | Jakab |
| 6,553,326 B1 | 4/2003 | Kirsch et al. |
| 6,584,301 B1 | 6/2003 | Bohn et al. |
| 6,593,884 B1 | 7/2003 | Gilboa et al. |
| 6,624,626 B2 | 9/2003 | Khalfin |
| 6,625,563 B2 | 9/2003 | Kirsch et al. |
| 6,636,757 B1 | 10/2003 | Jascob et al. |
| 6,656,135 B2 | 12/2003 | Zogbi et al. |
| 6,667,612 B2 | 12/2003 | Duret |
| 6,687,531 B1 | 2/2004 | Ferre et al. |
| 6,697,664 B2 | 2/2004 | Kienzle, III et al. |
| 6,701,179 B1 | 3/2004 | Martinelli et al. |
| 6,711,429 B1 | 3/2004 | Gilboa et al. |
| 6,738,656 B1 | 5/2004 | Ferre et al. |
| 6,754,596 B2 | 6/2004 | Ashe |
| 6,762,600 B2 | 7/2004 | Khalfin |
| 6,774,624 B2 | 8/2004 | Anderson et al. |
| 6,783,536 B2 | 8/2004 | Vilsmeier et al. |
| 6,784,660 B2 | 8/2004 | Ashe |
| 6,803,757 B2 | 10/2004 | Slates |
| 6,812,842 B2 | 11/2004 | Dimmer |
| 6,833,814 B2 | 12/2004 | Gilboa et al. |
| 6,836,745 B2 | 12/2004 | Seiler et al. |
| 6,838,873 B2 | 1/2005 | James et al. |
| 6,856,823 B2 | 2/2005 | Ashe |
| 6,856,826 B2 | 2/2005 | Seeley et al. |
| 6,856,827 B2 | 2/2005 | Seeley et al. |
| 6,887,245 B2 | 5/2005 | Kienzle, III et al. |
| 6,934,575 B2 | 8/2005 | Ferre et al. |
| 6,968,846 B2 | 11/2005 | Viswanathan |
| 6,980,921 B2 | 12/2005 | Anderson et al. |
| 7,015,859 B2 | 3/2006 | Anderson |
| 7,096,148 B2 | 8/2006 | Anderson et al. |
| 7,097,357 B2 | 8/2006 | Johnson et al. |
| 7,139,601 B2 | 11/2006 | Bucholz et al. |
| 7,153,297 B2 | 12/2006 | Peterson |
| 7,153,308 B2 | 12/2006 | Peterson |
| 7,158,754 B2 | 1/2007 | Anderson |
| 7,809,421 B1 * | 10/2010 | Govari .......................... 600/407 |
| 2001/0045826 A1 | 11/2001 | Schneider |
| 2001/0047133 A1 | 11/2001 | Gilboa et al. |
| 2002/0045812 A1 | 4/2002 | Ben-Haim et al. |
| 2003/0201767 A1 | 10/2003 | Khalfin |
| 2004/0011365 A1 | 1/2004 | Govari et al. |
| 2004/0068178 A1 | 4/2004 | Govari |
| 2004/0073228 A1 | 4/2004 | Kienzle, III et al. |
| 2004/0077940 A1 | 4/2004 | Kienzle, III et al. |
| 2004/0102696 A1 | 5/2004 | Govari |
| 2004/0207389 A1 | 10/2004 | Nieminen et al. |
| 2005/0012597 A1 | 1/2005 | Anderson |
| 2005/0049485 A1 | 3/2005 | Harmon et al. |
| 2005/0059883 A1 | 3/2005 | Peterson |
| 2005/0062469 A1 * | 3/2005 | Anderson ................ 324/207.17 |
| 2005/0065433 A1 | 3/2005 | Anderson |
| 2005/0104776 A1 | 5/2005 | Anderson |
| 2005/0107687 A1 | 5/2005 | Anderson |
| 2005/0222793 A1 | 10/2005 | Lloyd et al. |
| 2005/0228270 A1 | 10/2005 | Lloyd et al. |
| 2005/0245821 A1 | 11/2005 | Govari et al. |
| 2005/0288574 A1 | 12/2005 | Thornton et al. |
| 2006/0020915 A1 | 1/2006 | Lloyd et al. |
| 2006/0025668 A1 | 2/2006 | Peterson et al. |
| 2006/0030771 A1 | 2/2006 | Levine et al. |
| 2006/0055712 A1 | 3/2006 | Anderson |
| 2006/0058604 A1 | 3/2006 | Avinash et al. |
| 2006/0079756 A1 | 4/2006 | Lloyd et al. |
| 2006/0106292 A1 | 5/2006 | Anderson |
| 2006/0115054 A1 | 6/2006 | Yatsenko et al. |
| 2006/0121849 A1 | 6/2006 | Anderson |
| 2006/0154604 A1 | 7/2006 | Anderson |
| 2006/0247511 A1 | 11/2006 | Anderson |
| 2006/0262029 A1 | 11/2006 | Anderson |
| 2006/0267759 A1 | 11/2006 | Levine |
| 2007/0055125 A1 | 3/2007 | Anderson et al. |
| 2007/0129629 A1 | 6/2007 | Beauregard et al. |
| 2007/0164895 A1 | 7/2007 | Anderson |
| 2007/0167744 A1 | 7/2007 | Beauregard et al. |
| 2007/0211927 A1 | 9/2007 | Groszmann et al. |
| 2007/0238980 A1 | 10/2007 | Anderson |

FOREIGN PATENT DOCUMENTS

| | | |
|---|---|---|
| WO | WO03086498 | 10/2003 |

* cited by examiner

COIL ARRANGEMENT FOR AN ELECTROMAGNETIC TRACKING SYSTEM

BACKGROUND OF THE INVENTION

This disclosure relates generally to an electromagnetic tracking system that uses electromagnetic fields to determine the position and orientation of an object, and more particularly to an asymmetrical coil arrangement for an electromagnetic tracking system.

Electromagnetic tracking systems have been used in various industries and applications to provide position and orientation information relating to objects. For example, electromagnetic tracking systems may be useful in aviation applications, motion sensing applications, retail applications, and medical applications. In medical applications, electromagnetic tracking systems have been used to provide an operator (e.g., a physician, surgeon, or other medical practitioner) with information to assist in the precise and rapid positioning of a medical device, implant or instrument located in or near a patient's body during image-guided surgery. An electromagnetic tracking system provides positioning and orientation information for a medical device, implant or instrument with respect to the patient or a reference coordinate system. An electromagnetic tracking system provides intraoperative tracking of the precise location of a medical device, implant or instrument in relation to multidimensional images of a patient's anatomy.

An electromagnetic tracking system uses visualization tools to provide a medical practitioner with co-registered views of a graphical representation of the medical device, implant or instrument with pre-operative or intraoperative images of the patient's anatomy. In other words, an electromagnetic tracking system allows a medical practitioner to visualize the patient's anatomy and track the position and orientation of a medical device, implant or instrument with respect to the patient's anatomy. As the medical device, implant or instrument is positioned with respect to the patient's anatomy, the displayed image is continuously updated to reflect the real-time position and orientation of the medical device, implant or instrument. The combination of the image and the representation of the tracked medical device, implant or instrument provide position and orientation information that allows a medical practitioner to manipulate a medical device, implant or instrument to a desired location with an accurate position and orientation.

Generally, an electromagnetic tracking system may include an electromagnetic transmitter with an array of one or more transmitter coils, an electromagnetic receiver with an array of one or more receiver coils, electronics to generate a current drive signal for the one or more transmitter coils and to measure the mutual inductances between transmitter and receiver coils, and a computer to calculate the position and orientation of the receiver coil array with the respect to the transmitter coil array, or vice versa. An alternating current drive signal is provided to each coil of the electromagnetic transmitter, generating an electromagnetic field being emitted from each coil of the electromagnetic transmitter. The electromagnetic field generated by each coil in the electromagnetic transmitter induces a voltage in each coil of the electromagnetic receiver. These voltages are indicative of the mutual inductances between the coils of the electromagnetic transmitter and the coils of the electromagnetic receiver. These voltages and mutual inductances are sent to a computer for processing. The computer uses these measured voltages and mutual inductances to calculate the position and orientation of the coils of the electromagnetic transmitter relative to the coils of the electromagnetic receiver, or the coils of the electromagnetic receiver relative to the coils of the electromagnetic transmitter, including six degrees of freedom (x, y, and z measurements, as well as roll, pitch and yaw angles).

Electromagnetic tracking systems may be limited by the number of degrees of freedom they are able to track. In general, the number of degrees of freedom that an electromagnetic tracking system is able to track and resolve depends on the number of transmitting and receiving coils in the system. For example, a system comprising a single transmitting coil and multiple receiver coils may track a device or instrument in only five degrees of freedom (x, y, and z coordinates, as well as pitch and yaw angles). The roll angle is not measurable. As will be appreciated, the magnetic field from a coil small enough to be approximated as a dipole is symmetrical about the axis of the coil (coil's roll axis). As a result, rotating the coil about the coil's axis (i.e., the degree of freedom commonly known as "roll") does not change the magnetic field. The processor performing the processing cannot resolve the rotational orientation (roll) of the coil. Consequently, only five degrees of freedom of position and orientation are trackable.

One approach of obtaining the roll angle measurement is to add another coil to the electromagnetic transmitter or electromagnetic receiver configuration. However, having two coils in close proximity may introduce "mutual inductance coupling" into the mix. Mutual inductance coupling between coils can negatively impact accuracy performance of an electromagnetic tracking system because cross-coupling currents cannot be accurately measured. Mutual inductance coupling between two coils permits the current in one coil to induce a voltage in the second coil, causing current flow in the second coil with the first coil's waveform. This unwanted current makes distinguishing the two coils' magnetic fields more difficult.

Therefore, there is a need for a coil arrangement for an electromagnetic transmitter or receiver assembly in an electromagnetic tracking system that provides maximum tracking accuracy and the ability to measure six degrees of freedom of the position and orientation of a medical device, implant or instrument.

BRIEF DESCRIPTION OF THE INVENTION

In an embodiment, an electromagnetic tracking system comprising at least one transmitter assembly with at least one transmitter coil; at least one receiver assembly with two receiver coils attachable to an object to be tracked, the two receiver coils spaced apart from each other and positioned asymmetrically with respect to each other, the at least one receiver assembly communicating with and receiving signals from the at least one transmitter assembly; and electronics coupled to and communicating with the at least one transmitter assembly and the at least one receiver assembly for calculating the position and orientation of the object to be tracked.

In an embodiment, an electromagnetic tracking system comprising at least one transmitter assembly with two transmitter coils attachable to an object to be tracked, the two transmitter coils spaced apart from each other and positioned asymmetrically with respect to each other; at least one receiver assembly with at least one receiver coil, the at least one receiver assembly communicating with and receiving signals from the at least one transmitter assembly; and electronics coupled to and communicating with the at least one transmitter assembly and the at least one receiver assembly for calculating the position and orientation of the object to be tracked.

In an embodiment, a transmitter assembly for an electromagnetic tracking system comprising a first large coil spaced apart from a second small coil, and the second small coil positioned asymmetrically with respect to the first large coil.

In an embodiment, a receiver assembly for an electromagnetic tracking system comprising a first large coil spaced apart from a second small coil, and the second small coil positioned asymmetrically with respect to the first large coil.

In an embodiment, a method of maximizing the tracking accuracy of an electromagnetic tracking system comprising attaching a first large coil and a second small coil to an object to be tracked; and determining the position and orientation of the object to be tracked.

Various other features, objects, and advantages of the invention will be made apparent to those skilled in the art from the accompanying drawings and detailed description thereof.

DETAILED DESCRIPTION OF THE INVENTION

Figure 1:
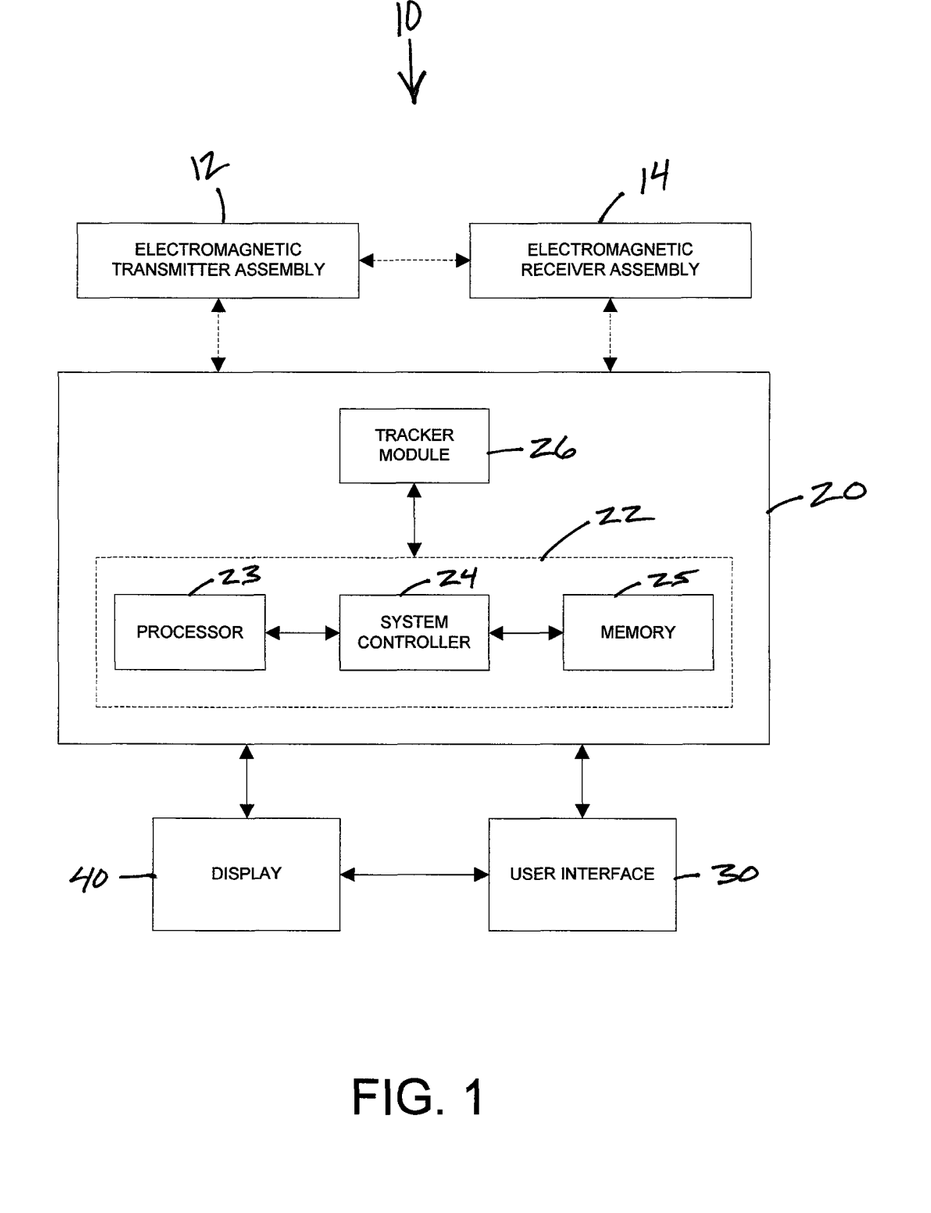
FIG. 1 is a block diagram illustrating an exemplary embodiment of an electromagnetic tracking system.

Referring now to the drawings, FIG. 1 is a block diagram illustrating an exemplary embodiment of an electromagnetic tracking system 10. The electromagnetic tracking system 10 comprises at least one electromagnetic transmitter assembly 12 with one or more transmitter coils and at least one electromagnetic receiver assembly 14 with one or more receiver coils. The transmitter or receiver coils are arranged to maximize the tracking accuracy and measure six degrees of freedom of the position and orientation of a medical device, implant or instrument.

The electromagnetic tracking system 10 further comprises a tracker workstation 20 coupled to and receiving data from the at least one electromagnetic transmitter assembly 12 and the at least one electromagnetic receiver assembly 14, a user interface 30 coupled to the tracker workstation 20, and a display 40 for visualizing imaging and tracking data. The tracker workstation 20 includes a tracking system computer 22 and a tracker module 26. The tracking system computer 22 includes at least one processor 23, a system controller 24 and memory 25.

The one or more coils of the electromagnetic transmitter and receiver assemblies 12, 14 may be built with various coil architectures. The one or more coils of the electromagnetic transmitter assembly 12 may be single coils, a pair of single coils, industry-standard-coil-architecture (ISCA) type coils, a pair of ISCA type coils, multiple coils, or an array of coils. The one or more coils of the electromagnetic receiver assembly 14 may be single coils, a pair of single coils, ISCA type coils, a pair of ISCA type coils, multiple coils, or an array of coils.

ISCA type coils are defined as three approximately collocated, approximately orthogonal, and approximately dipole coils. Therefore, ISCA electromagnetic transmitter and receiver coils would include three approximately collocated, approximately orthogonal, and approximately dipole coils for the transmitter assembly and three approximately collocated, approximately orthogonal, and approximately dipole coils for the receiver assembly. In other words, an ISCA configuration for the electromagnetic transmitter and receiver assemblies would include a three-axis dipole coil transmitter and a three-axis dipole coil receiver. In the ISCA configuration, the transmitter coils and the receiver coils are configured such that the three coils (i.e., coil trios) exhibit the same effective area, are oriented orthogonally to one another, and are centered at the same point.

In an exemplary embodiment, the one or more coils of the at least one electromagnetic transmitter assembly 12 may be characterized as single dipole coils and emit magnetic fields when a current is passed through the coils. Those skilled in the art will appreciate that multiple electromagnetic field generating coils may be used in coordination to generate multiple magnetic fields. Similar to the at least one electromagnetic transmitter assembly 12, the one or more coils of the at least one electromagnetic receiver assembly 14 may be characterized as single dipole coils and detect the magnetic fields emitted by the at least one electromagnetic transmitter assembly 12. When a current is applied to the one or more coils of the at least one electromagnetic transmitter assembly 12, the magnetic fields generated by the coils may induce a voltage into each coil of the at least one electromagnetic receiver assembly 14. The induced voltage is indicative of the mutual inductance between the one or more coils of the at least one electromagnetic transmitter assembly 12. Thus, the induced voltage across each coil of the at least one electromagnetic receiver assembly 14 is detected and processed to determine the mutual inductance between each coil of the at least one electromagnetic transmitter assembly 12 and each coil of the at least one electromagnetic receiver assembly 14.

The magnetic field measurements may be used to calculate the position and orientation of the at least one electromagnetic transmitter assembly 12 with respect to the at least one electromagnetic receiver assembly 14, or vice versa according to any suitable method or system. The detected magnetic field measurements are digitized by electronics that may be included with the at least one electromagnetic receiver assembly 14 or the tracker module 26. The magnetic field measurements or digitized signals may be transmitted from the at least one electromagnetic receiver assembly 14 to the tracking system computer 22 using wired or wireless communication protocols and interfaces. The digitized signals received by the tracking system computer 22 represent magnetic field information detected by the at least one electromagnetic receiver assembly 14. The digitized signals are used to calculate position and orientation information of the at least one electromagnetic transmitter assembly 12 or the at least one electromagnetic receiver assembly 14.

The position and orientation information is used to register the location of the at least one electromagnetic receiver assembly 14 or the at least one electromagnetic transmitter assembly 12 to acquired imaging data from an imaging system. The position and orientation data is visualized on the display 40, showing in real-time the location of the at least one electromagnetic transmitter assembly 12 or the at least one electromagnetic receiver assembly 14 on pre-acquired or real-time images from the imaging system. The acquired imaging data may be from a computed tomography (CT) imaging system, a magnetic resonance (MR) imaging system, a positron emission tomography (PET) imaging system, an ultrasound imaging system, an X-ray imaging system, or any suitable combination thereof. All six degrees of freedom (three of position (x, y, z) and three of orientation (roll, pitch, yaw)) of the at least one electromagnetic receiver assembly 14 or the at least one electromagnetic transmitter assembly 12 may be determined and tracked.

In an exemplary embodiment, the one or more coils of the electromagnetic transmitter and receiver assemblies 12, 14 are either precisely manufactured or precisely characterized during manufacture to obtain mathematical models of the one or more coils in the electromagnetic transmitter and receiver assemblies 12, 14. From the magnetic field measurements and mathematical models of the one or more coils, the position and orientation of the at least one electromagnetic receiver assembly 14 with respect to the at least one electromagnetic transmitter assembly 12 may be determined. Alternatively, the position and orientation of the at least one electromagnetic transmitter assembly 12 with respect to the at least one electromagnetic receiver assembly 14 may be determined.

In an exemplary embodiment, the at least one electromagnetic transmitter assembly 12 may be a battery-powered wireless transmitter assembly, a passive transmitter assembly, or a wired transmitter assembly. In an exemplary embodiment, the at least one electromagnetic receiver assembly 14 may be a battery-powered wireless receiver assembly, a passive receiver assembly, or a wired receiver assembly.

In an exemplary embodiment, the tracker module 26 may include drive circuitry configured to provide a drive current to each coil of the at least one electromagnetic transmitter assembly 12. By way of example, a drive current may be supplied by the drive circuitry to energize a coil of the at least one electromagnetic transmitter assembly 12, and thereby generate an electromagnetic field that is detected by a coil of the at least one electromagnetic receiver assembly 14. The drive current may be comprised of a periodic waveform with a given frequency (e.g., a sine wave, cosine wave or other periodic signal). The drive current supplied to a coil will generate an electromagnetic field at the same frequency as the drive current. The electromagnetic field generated by a coil of the at least one electromagnetic transmitter assembly 12 induces a voltage indicative of the mutual inductance in a coil of the at least one electromagnetic receiver assembly 14. In an exemplary embodiment, the tracker module 26 may include receiver data acquisition circuitry for receiving voltage and mutual inductance data from the at least one electromagnetic receiver assembly 14.

In an exemplary embodiment, the tracking system computer 22 may include at least one processor 23, such as a digital signal processor, a CPU, or the like. The processor 23 may process measured voltage and mutual inductance data from the at least one electromagnetic receiver assembly 14 to track the position and orientation of the at least one electromagnetic transmitter assembly 12 or the at least one electromagnetic receiver assembly 14.

The at least one processor 23 may implement any suitable algorithm(s) to use the measured voltage signal indicative of the mutual inductance to calculate the position and orientation of the at least one electromagnetic receiver assembly 14 relative to the at least one electromagnetic transmitter assembly 12, or the at least one electromagnetic transmitter assembly 12 relative to the at least one electromagnetic receiver assembly 14. For example, the at least one processor 23 may use ratios of mutual inductance between each coil of the at least one electromagnetic receiver assembly 14 and each coil of the at least one electromagnetic transmitter assembly 12 to triangulate the relative positions of the coils. The at least one processor 23 may then use these relative positions to calculate the position and orientation of the at least one electromagnetic transmitter assembly 12 or the at least one electromagnetic receiver assembly 14.

In an exemplary embodiment, the tracking system computer 22 may include a system controller 24. The system controller 24 may control operations of the electromagnetic tracking system 10.

In an exemplary embodiment, the tracking system computer 22 may include memory 25, which may be any processor-readable media that is accessible by the components of the tracker workstation 20. In an exemplary embodiment, the memory 25 may be either volatile or non-volatile media. In an exemplary embodiment, the memory 25 may be either removable or non-removable media. Examples of processor-readable media may include (by way of example and not limitation): RAM (Random Access Memory), ROM (Read Only Memory), registers, cache, flash memory, storage devices, memory sticks, floppy disks, hard drives, CD-ROM, DVD-ROM, network storage, and the like.

In an exemplary embodiment, the user interface 30 may include devices to facilitate the exchange of data and workflow between the system and the user. In an exemplary embodiment, the user interface 30 may include a keyboard, a mouse, a joystick, buttons, a touch screen display, or other devices providing user-selectable options, for example. In an exemplary embodiment, the user interface 30 may also include a printer or other peripheral devices.

In an exemplary embodiment, the display 40 may be used for visualizing the position and orientation of a tracked object with respect to a processed image from an imaging system.

In an exemplary embodiment, the at least one electromagnetic receiver assembly 14 may be attached to a medical device, implant or instrument 16 to be tracked and the at least one electromagnetic transmitter assembly 12 may generate at least one electromagnetic field to be received by the at least one electromagnetic receiver assembly 14. The electromagnetic tracking system 10, may track the position and orientation of the medical device, implant or instrument 16 during a medical procedure.

In an exemplary embodiment, the at least one electromagnetic transmitter assembly 12 may be attached to a medical device, implant or instrument 16 to be tracked and the at least one electromagnetic receiver assembly 14 may be positioned within at least one electromagnetic field generated by the at least one electromagnetic transmitter assembly 12. The electromagnetic tracking system 10 enables a medical professional to continually track the position and orientation of the medical device, implant or instrument 16 during a medical procedure.

In an exemplary embodiment, the at least one electromagnetic transmitter and receiver assemblies 12, 14 may be wireless, with the coils being driven self-contained circuitry, data acquisitions being performed by self-contained circuitry, and power being provided by a self-contained power source.

Notwithstanding the description of the exemplary embodiment of the electromagnetic tracking system 10 illustrated FIG. 1, alternative system architectures may be substituted without departing from the scope of the invention.

Figure 2:
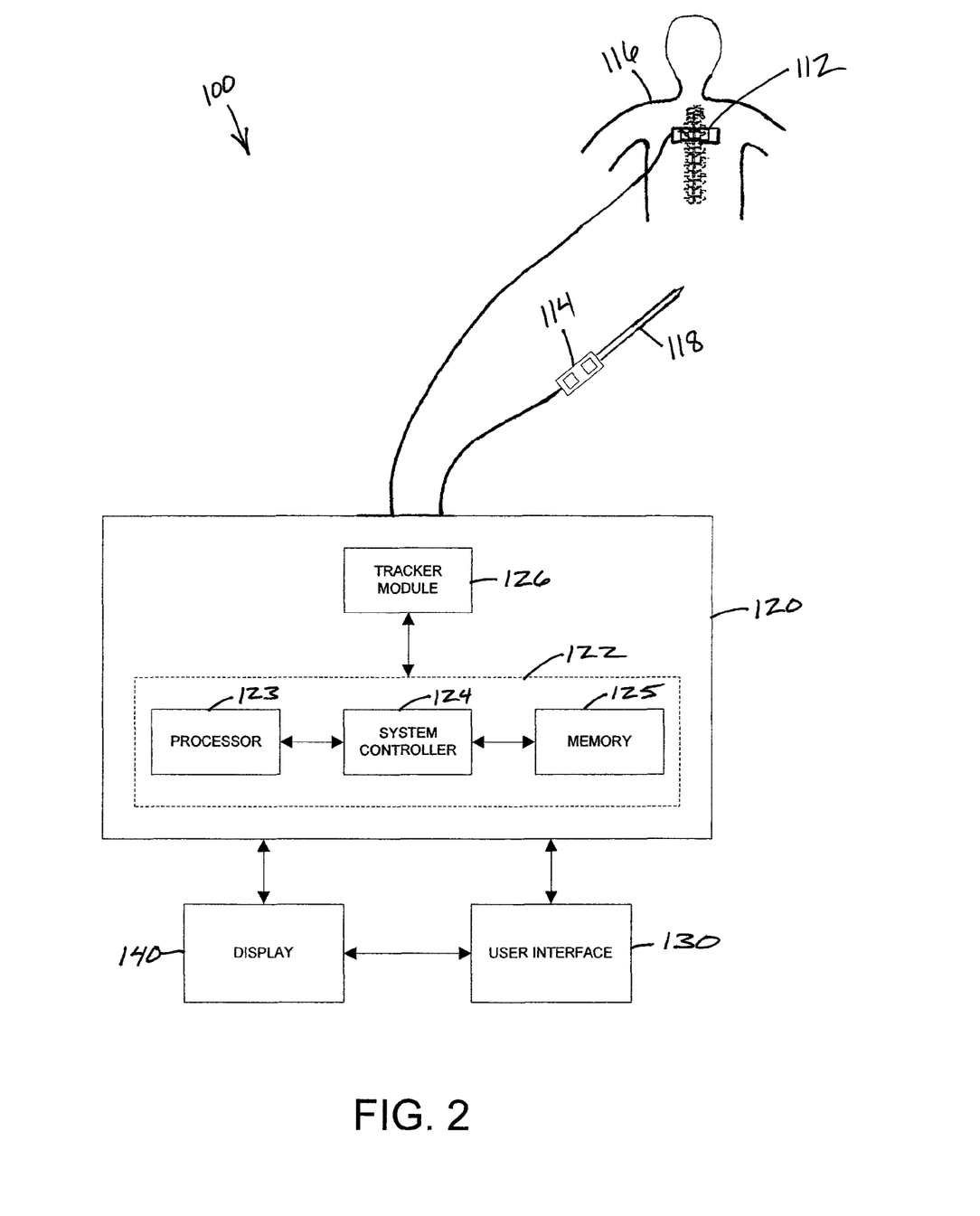
FIG. 2 is a diagram illustrating an exemplary embodiment of an electromagnetic tracking system.

FIG. 2 is a diagram illustrating an exemplary embodiment of an electromagnetic tracking system 100. The electromagnetic tracking system 100 comprises at least one electromagnetic transmitter assembly 112 with one or more coils positioned proximate to a patient 116 in a surgical field of interest and at least one electromagnetic receiver assembly 114 with two coils attachable to a trackable medical device, implant or instrument 118 to be tracked. The electromagnetic tracking system 100 enables a medical professional to continually track the position and orientation of the medical device, implant or instrument 118 during a medical procedure.

The two coils of the at least one electromagnetic receiver assembly 114 may be attachable to a proximal end of the medical device, implant or instrument 118, to track the position and orientation of the tip or distal end of the medical device, implant or instrument 118. To provide maximum accuracy, the two coils include a first large coil with its axis aligned with the tip or distal end of the medical device, implant or instrument 118 and a second small coil positioned asymmetrically with respect to the first large coil. The first large coil provides good medical device, implant or instrument 118 axis resolution.

The electromagnetic tracking system 100 further comprises a tracker workstation 120 coupled to and receiving data from the at least one electromagnetic transmitter assembly 112 and the at least one electromagnetic receiver assembly 114, a user interface 130 coupled to the tracker workstation 120, and a display 140 for visualizing imaging and tracking data. The tracker workstation 120 includes a tracking system computer 122 and a tracker module 126. The tracking system computer 122 includes at least one processor 123, a system controller 124 and memory 125.

In an exemplary embodiment, the one or more coils of the at least one electromagnetic transmitter assembly 112 may be characterized as single dipole coils and generate one or more magnetic fields when a current is applied to the one or more coils. The two coils of the at least one electromagnetic receiver assembly 114 may also be characterized as single dipole coils and detect the one or more magnetic fields generated by the at least one electromagnetic transmitter assembly 112. The one or more magnetic fields generated by the one or more coils of the at least one electromagnetic transmitter assembly 112 may induce a voltage into each coil of the at least one electromagnetic receiver assembly 114. The induced voltage is indicative of the mutual inductance between the one or more coils of the at least one electromagnetic transmitter assembly 112. Thus, the induced voltage across each coil of the at least one electromagnetic receiver assembly 114 is detected and processed to determine the mutual inductance between each coil of the at least one electromagnetic transmitter assembly 112 and each coil of the at least one electromagnetic receiver assembly 114.

The magnetic field measurements can be used to calculate the position and orientation of the medical device, implant or instrument 118 according to any suitable method or system. The detected magnetic field measurements are digitized by electronics that may be included with the at least one electromagnetic receiver assembly 114 or the tracker module 126. The magnetic field measurements or digitized signals may be transmitted from the at least one electromagnetic receiver assembly 114 to the tracking system computer 122 using wired or wireless communication protocols and interfaces. The digitized signals received by the tracking system computer 122 represent magnetic field information detected by the at least one electromagnetic receiver assembly 114. The digitized signals are used to calculate position and orientation information of the at least one electromagnetic transmitter assembly 112 or the at least one electromagnetic receiver assembly 114.

The position and orientation information is used to register the location of the medical device, implant or instrument 118 to acquired imaging data from an imaging system. The position and orientation data is visualized on the display 140, showing in real-time the location of the medical device, implant or instrument 118 on pre-acquired or real-time images from the imaging system. In other words, the display 140 may be configured to show the real-time position and orientation of the medical device, implant or instrument 118 on a registered image of the patient's 116 anatomy. The acquired imaging data may be from a CT imaging system, a MR imaging system, a PET imaging system, an ultrasound imaging system, an X-ray imaging system, or any suitable combination thereof. All six degrees of freedom (three of position (x, y, z) and three of orientation (roll, pitch, yaw)) of the medical device, implant or instrument 118 may be determined and tracked.

In an exemplary embodiment, at least one electromagnetic receiver assembly 114 with one or more coils positioned proximate to a patient 116 in a surgical field of interest and at least one electromagnetic transmitter assembly 112 with two coils attachable to a trackable medical device, implant or instrument 118 to be tracked. The electromagnetic tracking system 100 enables a medical professional to continually track the position and orientation of the medical device, implant or instrument 118 during a medical procedure.

In an exemplary embodiment, the at least one electromagnetic transmitter assembly 112 may be a battery-powered wireless transmitter assembly, a passive transmitter assembly, or a wired transmitter assembly. In an exemplary embodiment, the at least one electromagnetic receiver assembly 114 may be a battery-powered wireless receiver assembly, a passive receiver assembly, or a wired receiver assembly.

In an exemplary embodiment, the at least one electromagnetic transmitter and receiver assemblies 112, 114 may be wireless, with the coils being driven by self-contained circuitry, data acquisitions being performed by self-contained circuitry, and power being provided by a self-contained power source.

The electromagnetic tracking system 100 is illustrated conceptually and may be implemented using any combination of dedicated hardware boards, digital signal processors, field programmable gate arrays, and processors. Alternatively, the tracker workstation 120 may be implemented using an off-the-shelf computer with a single processor or multiple processors, with the functional operations distributed between processors. As an example, it may be desirable to have a dedicated processor for position and orientation operations as well as a processor for visualization operations.

Figure 3:
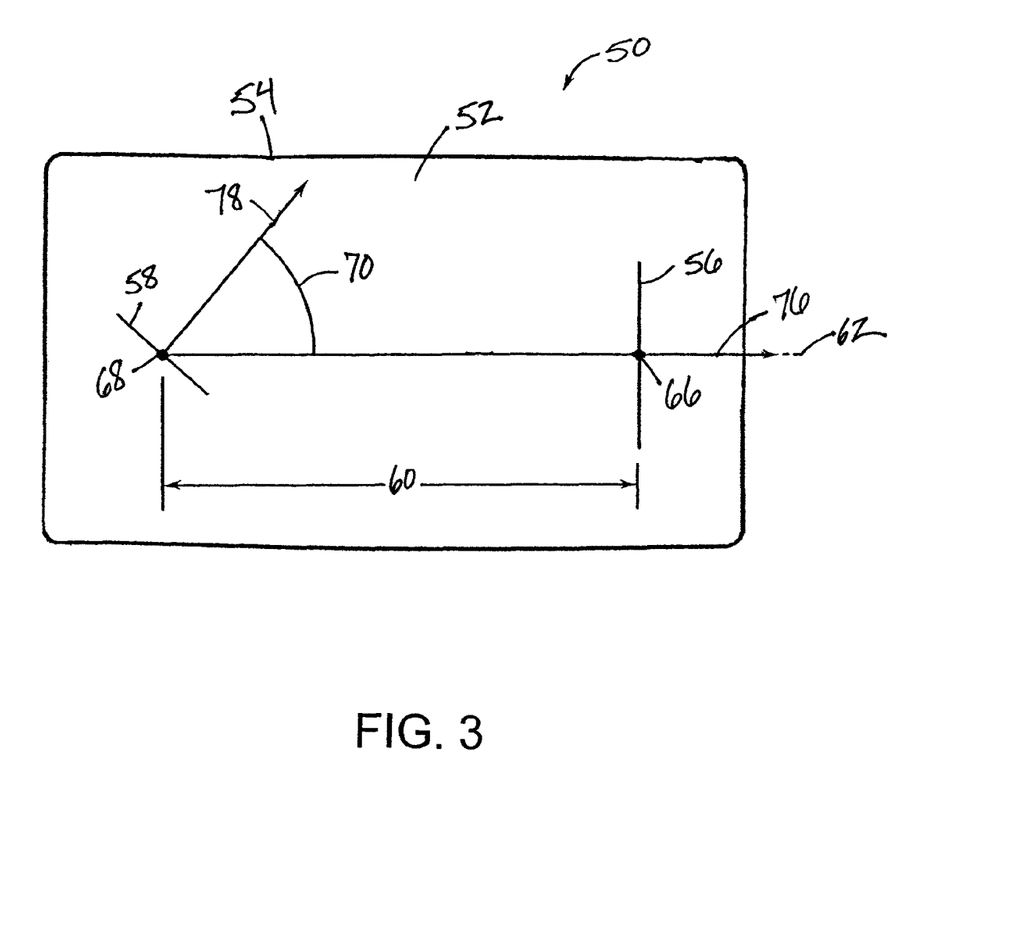
FIG. 3 is a schematic diagram illustrating an exemplary embodiment of an electromagnetic transmitter or receiver coil arrangement for an electromagnetic tracking system.

FIG. 3 is a schematic diagram illustrating an exemplary embodiment of an electromagnetic transmitter or receiver coil arrangement 50 for an electromagnetic tracking system. The electromagnetic transmitter or receiver coil arrangement 50 includes an asymmetrical two coil array 52 enclosed within a housing 54. The two coil array 52 includes a first large coil 56 and a second small coil 58 that are spaced apart from each other by a separation distance 60. The second small coil 58 is positioned asymmetrically with respect to the first large coil 56. The housing 54 provides for rigidly mounting the second small coil 58 with respect to the first large coil 56. The housing 54 may take the form of an enclosure coupled to the body of a medical device, implant or instrument. The first large coil 56 and the second small coil 58 are configured in a distinctive geometric arrangement relative to each other to provide maximum accuracy and allow for all six degrees of freedom (x. y, z, roll, pitch, yaw) to be tracked.

The first large coil 56 and the second small coil 58 are angled at different orientations relative to a longitudinal axis 62 running from the center 66 of the first large coil 56 to the center 68 of the second small coil 58. For example, the second small coil 58 may be angled at an angle 70 from the longitudinal axis 62, and the first large coil 56 may be in-line with the longitudinal axis 62. The second small coil's center 68 is approximately on the large coil's axis 76. The small coil's axis 78 is angled, neither perpendicular to nor parallel with the large coil's axis 76. The axes 76, 78 of the two coils 56, 58 are pointed in different directions.

The first large coil 56 provides a large signal-to-noise ratio, and thus good accuracy of five degrees of freedom of the position and orientation of a medical device, implant or instrument being tracked, excluding roll about the first large coil's axis 76. The second small coil 58 provides determination of the first large coil's roll with low accuracy. The low accuracy is enough because the roll component of the first large coil's tip-offset vector is small.

In an exemplary embodiment, if the transmitter or receiver coil array 52 is wireless, the phases of the coils' signal waves are tracked and are subjected to a 180-degree ambiguity. This has the effect that each tracked orientation vector may or may not be multiplied by −1. In other words, the sign of the magnetic moment or gain of the coils are not known.

The mechanical asymmetry of the arrangement of the two coils permits determination of the sign of the magnetic moment or gain of the coils. For example, the second small coil allows determining the sign of the magnetic moment or gain of the first large coil. The tracked positions and the known mechanical relationship between the two coils may be used to calculate expected orientation vectors of the two coils. These two estimated orientation vectors will individually be approximately the same as or approximately the opposite-direction to the tracked orientation vectors. Reversing the direction of the tracked orientations vectors is needed to make the tracked orientation vectors agree with the expected orientation vectors.

Figure 4:
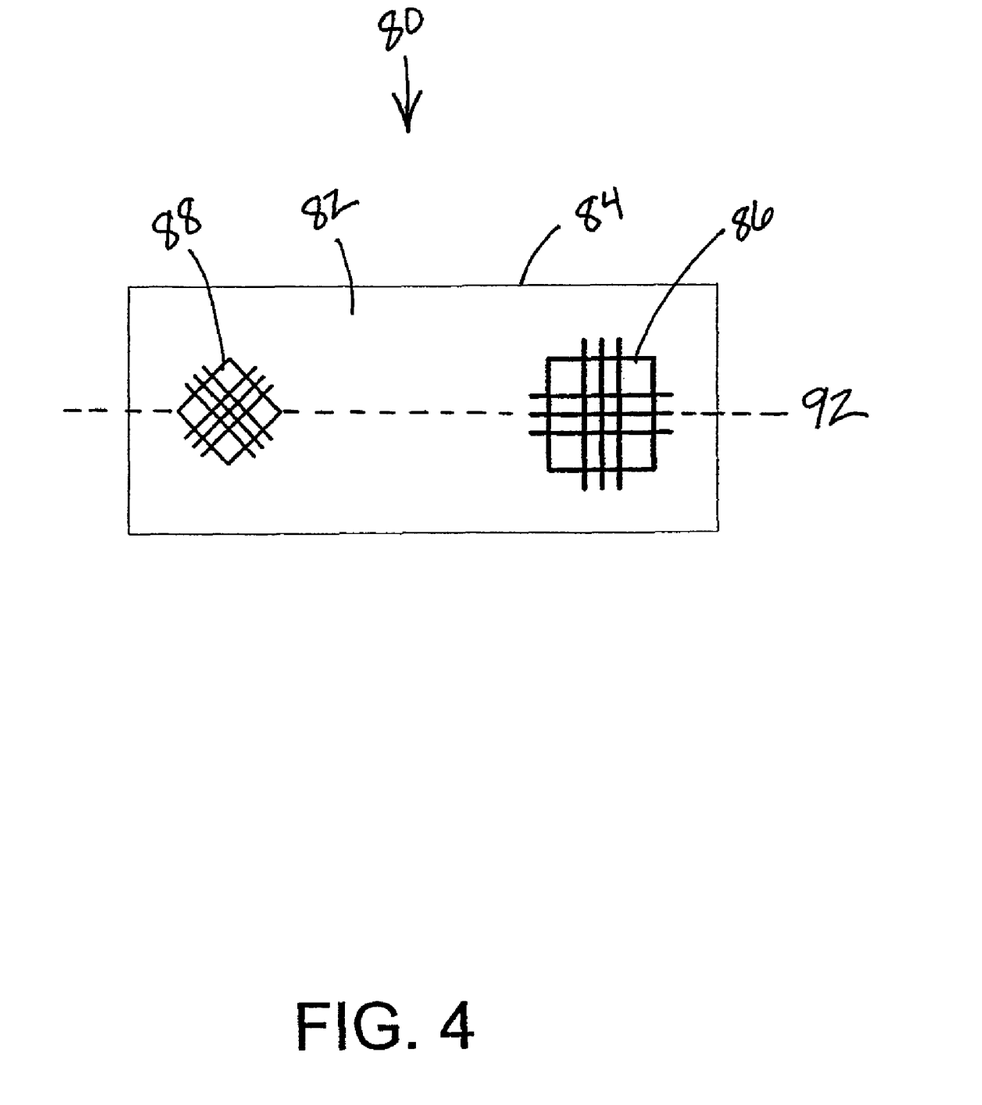
FIG. 4 is a schematic diagram illustrating an exemplary embodiment of an electromagnetic transmitter or receiver coil arrangement for an electromagnetic tracking system.

FIG. 4 is a schematic diagram illustrating an exemplary embodiment of an electromagnetic transmitter or receiver coil arrangement 80 for an electromagnetic tracking system. The electromagnetic transmitter or receiver coil arrangement 80 includes an asymmetrical two coil array 82 enclosed within a housing 84. The two coil array 82 includes a first large coil 86 and a second small coil 88 that are spaced apart from each other with the second small coil 88 positioned asymmetrically with respect to the first large coil 86. The housing 84 provides for rigidly mounting the second small coil 88 with respect to the first large coil 86. The housing 84 may take the form of an enclosure coupled to the body of a medical device, implant or instrument. The first large coil 86 and the second small coil 88 are arranged asymmetrically to each other to provide maximum accuracy and allow for all six degrees of freedom (x. y, z, roll, pitch, yaw) of position and orientation of a medical device, implant or instrument to be tracked. The first large coil 86 and the second small coil 88 are angled at different orientations. The angle of the second small coil 88 with respect to a longitudinal axis 92 extending through the centers of the coils 86, 88 is neither perpendicular to nor parallel with the angle of the first large coil 86 with respect to the longitudinal axis 92.

In an exemplary embodiment, the two coils 86, 88 may be ISCA type coils, each with three approximately collocated, approximately orthogonal, and approximately dipole coils (i.e., coil trios). The coil trios exhibit the same effective area, are oriented orthogonally to one another, and are centered at the same point.

In an exemplary embodiment, a method of maximizing the tracking accuracy of an electromagnetic tracking system comprises attaching a first large coil and a second small coil to an object to be tracked, and determining the position and orientation of the object to be tracked. The second small coil may be positioned asymmetrically with respect to the first large coil. The step of determining the position and orientation of the object to be tracked may include applying a drive current to at least one coil of a transmitter assembly, measuring the magnetic field generated by the at least one coil of the transmitter assembly and received by at least one coil of a receiver assembly, and using the magnetic field measurements to calculate the position and orientation of the object to be tracked. The object to be tracked may be a medical device, implant or instrument.

Several embodiments are described above with reference to drawings. These drawings illustrate certain details of exemplary embodiments that implement the systems, methods and computer programs of this disclosure. However, the drawings should not be construed as imposing any limitations associated with features shown in the drawings.

Certain embodiments may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the system might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer.

While the invention has been described with reference to various embodiments, those skilled in the art will appreciate that certain substitutions, alterations and omissions may be made to the embodiments without departing from the spirit of the invention. Accordingly, the foregoing description is meant to be exemplary only, and should not limit the scope of the disclosure as set forth in the following claims.

What is claimed is:

1. An electromagnetic tracking system, comprising:
   at least one transmitter assembly with at least one transmitter coil element;
   at least one receiver assembly with two receiver coil elements attachable to an object to be tracked, the two receiver coil elements spaced apart from each other and positioned asymmetrically with respect to each other so that an axis of a first receiver coil element is neither perpendicular to nor parallel with an axis of a second receiver coil element within the same assembly, the at least one receiver assembly communicating with and receiving signals from the at least one transmitter assembly; and electronics coupled to and communicating with the at least one transmitter assembly and the at least one receiver assembly for calculating the position and orientation of the object to be tracked.

2. The electromagnetic tracking system of claim 1, wherein the first and second receiver coil elements respectively include a first large coil element and a second small coil element.

3. The electromagnetic tracking system of claim 2, wherein the first large coil element is aligned with a distal end of a medical instrument and the second small coil element is positioned asymmetrically with respect to the first large coil element.

4. The electromagnetic tracking system of claim 1, wherein the at least one receiver assembly is attachable to a proximal end of a medical instrument to track the position and orientation of a distal end of the medical instrument.

5. The electromagnetic tracking system of claim 1, wherein the two receiver coil elements are angled at different angles with respect to each other.

6. The electromagnetic tracking system of claim 2, wherein the first large coil element is centered on a longitudinal axis and angled at a first angle with respect to the longitudinal axis and the second small coil element is centered on the longitudinal axis and angled at a second angle with respect to the longitudinal axis.

7. The electromagnetic tracking system of claim 1, wherein a center of the second receiver coil element is on the large receiver coil element's axis.

8. The electromagnetic tracking system of claim 2, wherein the second small coil element is positioned asymmetrically with respect to the first large coil element.

9. The electromagnetic tracking system of claim 1, wherein the object to be tracked is a medical device, implant or instrument.

10. An electromagnetic tracking system, comprising:
at least one transmitter assembly with two transmitter coil elements attachable to an object to be tracked, the two transmitter coil elements spaced apart from each other and positioned asymmetrically with respect to each other so that an axis of a first transmitter coil element is neither perpendicular to nor parallel with an axis of a second transmitter coil element within the same assembly;
at least one receiver assembly with at least one receiver coil element, the at least one receiver assembly communicating with and receiving signals from the at least one transmitter assembly; and
electronics coupled to and communicating with the at least one transmitter assembly and the at least one receiver assembly for calculating the position and orientation of the object to be tracked.

11. The electromagnetic tracking system of claim 10, wherein the first and second transmitter coil elements respectively include a first large coil element and a second small coil element, and wherein the second small coil element is positioned asymmetrically with respect to the first large coil element.

12. The electromagnetic tracking system of claim 11, wherein the first large coil element is aligned with a distal end of a medical instrument and the second small coil element is positioned asymmetrically with respect to the first large coil element.

13. The electromagnetic tracking system of claim 10, wherein the at least one receiver assembly is attachable to a proximal end of a medical instrument to track the position and orientation of a distal end of the medical instrument.

14. The electromagnetic tracking system of claim 10, wherein the object to be tracked is a medical device, implant or instrument.

15. A transmitter assembly for an electromagnetic tracking system, comprising a first large coil element spaced apart from a second small coil element, and the second small coil element positioned asymmetrically with respect to the first large coil element so that an axis of the first large coil element is neither perpendicular to nor parallel with an axis of the second small coil element.

16. The transmitter assembly of claim 15, wherein the first large coil element and the second small coil element is coupled to an object to be tracked.

17. The transmitter assembly of claim 16, wherein the object to be tracked is a medical device, implant or instrument.

18. A receiver assembly for an electromagnetic tracking system comprising a first large coil element spaced apart from a second small coil element, and the second small coil element positioned asymmetrically with respect to the first large coil element so that an axis of the first large coil element is neither perpendicular to nor parallel with an axis of the second small coil element within the same assembly.

19. The receiver assembly of claim 18, wherein the first large coil element and the second small coil element is coupled to an object to be tracked.

20. The receiver assembly of claim 19, wherein the object to be tracked is a medical device, implant or instrument.

21. A method of maximizing the tracking accuracy of an electromagnetic tracking system, comprising:
attaching a first large coil element and a second small coil element to an object to be tracked so that an axis of the first large coil element is neither perpendicular to nor parallel with an axis of a second small coil element within the same assembly; and
determining the position and orientation of the object to be tracked.

22. The method of claim 21, wherein the second small coil element is positioned asymmetrically with respect to the first large coil element.

23. The method of claim 21, wherein the step of determining the position and orientation of the object to be tracked includes applying a drive current to at least one coil element of a transmitter assembly, measuring the magnetic field generated by the at least one coil element of the transmitter assembly and received by at least one coil element of a receiver assembly, and using the magnetic field measurements to calculate the position and orientation of the object to be tracked.

24. The method of claim 21, wherein the object to be tracked is a medical device, implant or instrument.

* * * * *

UNITED STATES PATENT AND TRADEMARK OFFICE
CERTIFICATE OF CORRECTION

| | | |
|---|---|---|
| PATENT NO. | : 8,391,952 B2 | Page 1 of 1 |
| APPLICATION NO. | : 11/870854 | |
| DATED | : March 5, 2013 | |
| INVENTOR(S) | : Peter Traneus Anderson | |

It is certified that error appears in the above-identified patent and that said Letters Patent is hereby corrected as shown below:

In the Specification

In Column 6, line 38, please delete "16".
In Column 6, line 42, please delete "16".
In Column 6, line 48, please delete "16".

Signed and Sealed this
Twenty-ninth Day of October, 2013

Teresa Stanek Rea
*Deputy Director of the United States Patent and Trademark Office*